US008568288B2

(12) United States Patent
Kaneshima et al.

(10) Patent No.: US 8,568,288 B2
(45) Date of Patent: Oct. 29, 2013

(54) SLIDE DEVICE, MECHANICAL SEAL, ROTARY DEVICE, PUMP AND AUXILIARY ARTIFICIAL HEART SYSTEM

(75) Inventors: Keiichiro Kaneshima, Suwa (JP); Takayuki Miyakoshi, Suwa (JP); Tomoya Kitano, Suwa (JP); Hideki Kanebako, Suwa (JP); Shinji Kobayashi, Suwa (JP); Koshi Adachi, Sendai (JP); Koki Kanda, Sendai (JP); Daisuke Suzuki, Sendai (JP)

(73) Assignees: Sun Medical Technology Research Corporation, Nagano (JP); Tohoku University, Miyagi (JP)

( * ) Notice: Subject to any disclaimer, the term of this patent is extended or adjusted under 35 U.S.C. 154(b) by 0 days.

(21) Appl. No.: 13/449,453

(22) Filed: Apr. 18, 2012

(65) Prior Publication Data
US 2013/0102834 A1 Apr. 25, 2013

(30) Foreign Application Priority Data
Oct. 22, 2011 (JP) .................................. 2011-232331

(51) Int. Cl.
*A61N 1/362* (2006.01)
(52) U.S. Cl.
USPC .......................................................... 600/16
(58) Field of Classification Search
USPC .................... 600/16; 428/34.1; 277/370, 644; 508/100
See application file for complete search history.

(56) References Cited

U.S. PATENT DOCUMENTS

| 2007/0090605 | A1* | 4/2007 | Grimanis et al. | 277/370 |
| 2007/0119246 | A1 | 5/2007 | Miyakoshi et al. | |
| 2009/0186783 | A1* | 7/2009 | Martin et al. | 508/100 |
| 2010/0259016 | A1* | 10/2010 | Halling | 277/644 |
| 2010/0272931 | A1* | 10/2010 | Stavlid | 428/34.1 |

FOREIGN PATENT DOCUMENTS

JP 2005-298528 A 10/2005

OTHER PUBLICATIONS

"Proceedings of JAST Tribilogy Conference", Tokyo, Japan, May 23-25, 2011, pp. 161-162.
H. Tagami, "Application cases; Mechanical seal", Tribiliogist, 1989, vol. 34, No. 2, pp. 140-143.

* cited by examiner

*Primary Examiner* — Robert N Wieland
(74) *Attorney, Agent, or Firm* — Lowe, Hauptman & Ham

(57) ABSTRACT

Provided is a slide device which can reduce a frictional force more than a conventional slide device when used in an aqueous liquid containing a blood component. In a slide device which includes: a fixed-side slide member having a slide surface; and a rotary-side slide member having a slide surface, the slide device being used in an aqueous liquid containing a blood component in a state where the slide surface of the fixed-side slide member and the slide surface of the rotary-side slide member face each other in an opposed manner, at least one of the fixed-side slide member and the rotary-side slide member is formed of a member which is made of a material which contains silicon and has hydrate of silicon oxide on the slide surface thereof.

7 Claims, 9 Drawing Sheets

FIG.10A SiC/SiC+running-in treatment
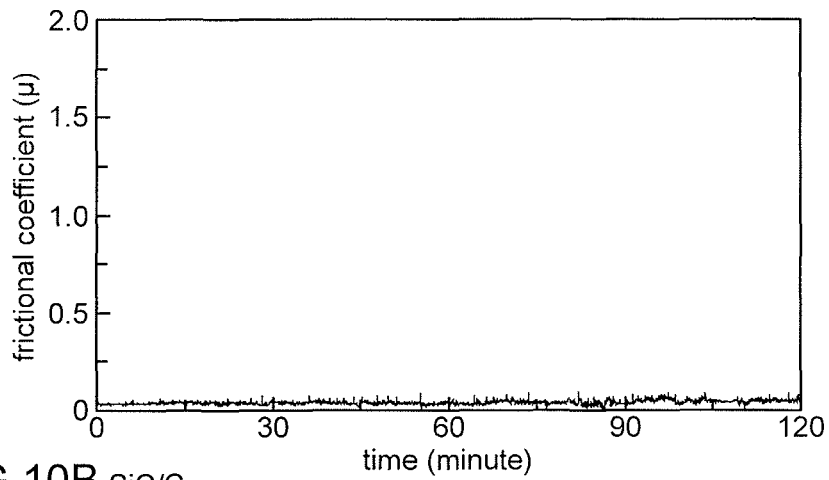
FIG.10B SiC/C
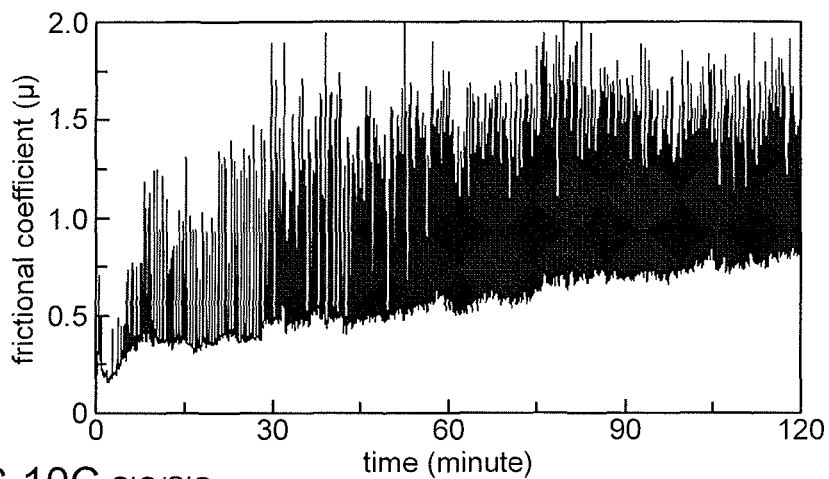
FIG.10C SiC/SiC
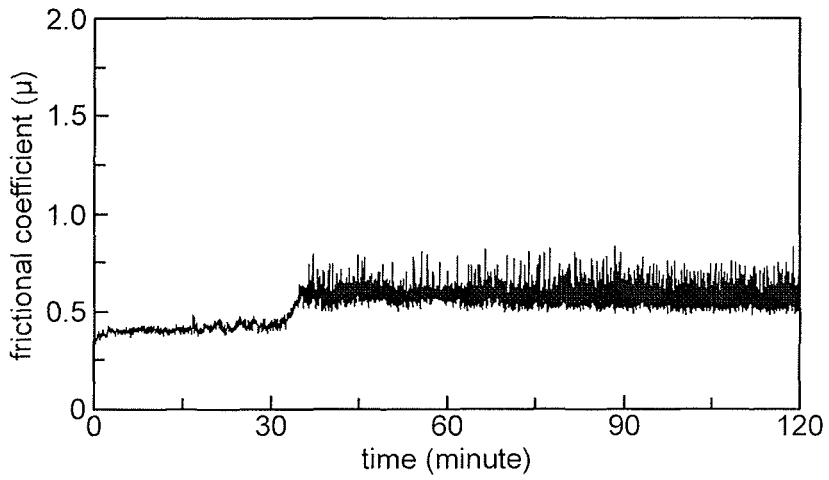

US 8,568,288 B2

SLIDE DEVICE, MECHANICAL SEAL, ROTARY DEVICE, PUMP AND AUXILIARY ARTIFICIAL HEART SYSTEM

RELATED APPLICATIONS

The present application is based on, and claims priority from, Japanese Application No. 2011-232331, filed Oct. 22, 2011, the disclosure of which is hereby incorporated by reference herein in its entirety.

TECHNICAL FIELD

The present invention relates to a slide device, a mechanical seal, a rotary device, a pump and an auxiliary artificial heart system.

BACKGROUND OF THE INVENTION

Pumps which impart a moving force to a liquid have been popularly used in various industrial fields. Among these pumps, as a pump which imparts a moving force to blood particularly, there has been conventionally known an auxiliary artificial heart pump (see patent document 1, for example).

FIG. 11 is a cross-sectional view of a conventional auxiliary artificial heart pump 900.

The conventional auxiliary artificial heart pump 900 includes a slide device 901 as shown in FIG. 11. The slide device 901 includes a fixed-side slide member 912 having a slide surface and a rotary-side slide member 922 having a slide surface, and the slide device 901 is used in a state where the slide surface of the fixed-side slide member 912 and the slide surface of the rotary-side slide member 922 face each other in an opposed manner. To further explain the slide device 901, the slide device 901 is a slide device which is used in blood in a state where the fixed-side slide member 912 and the rotary-side slide member 922 are brought into contact with each other. The fixed-side slide member 912 is made of silicon carbide, for example. The rotary-side slide member 922 is made of carbon, for example.

The fixed-side slide member 912 is also a member which constitutes a portion of a fixed part 910.

The rotary-side slide member 922 is also a member which constitutes a portion of a rotary part 920. The rotary part 920 includes, besides the rotary-side slide member 922, an impeller 926 and a rotary shaft 928. A drive force (a rotational force) is imparted to the rotary shaft 928 by a drive part 930 so that the whole rotary part 920 is rotated.

The slide device 901 also plays a role of a mechanical seal which prevents the intrusion of a blood component into the drive part 930 or the like of the auxiliary artificial heart pump 900. Although the indication of parts in the drawing using symbols and the detailed explanation of the parts are omitted, the auxiliary artificial heart pump 900 additionally includes a cool sealing liquid circulating part 940 (the symbol not shown in the drawing). The cool sealing liquid circulating part 940 circulates a cool sealing liquid (also referred to as "purge liquid") which performs functions such as the lubrication of the inside of the auxiliary artificial heart pump 900, the cooling of inside of the auxiliary artificial heart pump 900, and the maintenance of sealing property of the inside of the auxiliary artificial heart pump 900.

Since the conventional auxiliary artificial heart pump 900 includes the above-mentioned slide device 901, the slide device ensures sliding between the fixed part and the rotary part so that the stable operation of the auxiliary artificial heart pump is ensured.

Patent document 1: JP-A-2005-269528

SUMMARY OF THE INVENTION

Task to be Solved by the Invention

In the technical field of auxiliary artificial heart pumps, there has been a demand for the further stable operation of the auxiliary artificial heart pumps. Such a demand is not limited to the technical field of auxiliary artificial heart pumps, and the demand also exists in a technical field of pumps for moving blood or an aqueous liquid in which a specific blood component is dispersed (hereinafter also referred to as "aqueous liquid containing a blood component") in the same manner. Inventors of the present invention have, to satisfy the above-mentioned demand, made extensive efforts to "reduce a frictional force of a slide device or a rotary device which a pump includes". This is because it is thought that the above-mentioned demand can be satisfied by reducing the frictional force of the slide device or the rotary device included in the pump.

The present invention has been made in view of the above-mentioned circumstances, and it is an object of the present invention to provide a slide device which can further reduce a frictional force compared to a conventional slide device when the slide device is used in an aqueous liquid containing a blood component. It is another object of the present invention to provide a mechanical seal which includes the slide device according to the present invention. It is still another object of the present invention to provide a rotary device which can further reduce a frictional force compared to a conventional rotary device when the rotary device is used in an aqueous liquid containing a blood component. It is further another object of the present invention to provide a pump which includes the mechanical seal or the rotary device of the present invention and an auxiliary artificial heart system.

Means for Solving the Task

The inventors of the present invention have paid attention to a fact that there is a case where when a slide device is used in an aqueous liquid containing a blood component, a blood component (for example, a protein component or a blood plasma) adheres to a slide surface so that a frictional force is increased. The adhesion per se of the blood component to the slide surface has been considered as a problem in the past, and as a measure to overcome this problem, for example, there has been proposed the structure (cool sealing structure) which can clean the slide surface using a cool sealing liquid (for example, pure water or a physiological salt solution) as described above.

However, to ensure the further stable operation of an auxiliary artificial heart pump, it is necessary for the slide device to further reduce a frictional force compared to a conventional slide device. In view of the above-mentioned circumstances, the inventors of the present invention have extensively studied the constitution which can make the adhesion of a blood component to a slide surface difficult, and have completed the present invention. The present invention is constituted of the following components.

(1) According to one aspect of the present invention, there is provided a slide device which includes: a fixed-side slide member having a slide surface and a rotary-side slide member having a slide surface, the slide device being used in an aqueous liquid containing a blood component in a state where the slide surface of the fixed-side slide member and the slide surface of the rotary-side slide member face each other in an opposed manner, wherein at least one of the fixed-side slide member and the rotary-side slide member is formed of "a member which is made of a material containing silicon and has hydrate of silicon oxide on the slide surface thereof (hereinafter referred to as a slide member made of a silicon-containing material)".

According to the slide device of the present invention, at least one of the fixed-side slide member and the rotary-side slide member is formed of the above-mentioned slide member made of a silicon-containing material and hence, as can be understood from experimental examples described later, "hydrate of silicon oxide which has high hydrophilicity" is formed on the slide surface. Accordingly, "a blood component having hydrophobicity in general" hardly adheres to the slide surface and thereby when the slide device is used in an aqueous liquid containing a blood component, the slide device can further reduce a frictional force compared to a conventional slide device.

According to the present invention, the blood from which the blood component is derived is not limited to human blood, and may be blood of various kinds of animals such as a mammal, a bird, a reptile or the like besides the human blood.

The slide device of the present invention may preferably be a slide device which is used in a state where a predetermined load is applied between the fixed-side slide member and the rotary-side slide member in the direction along a rotation axis of the rotary-side slide member. The present invention is preferably applicable to the slide device having such a constitution (so-called thrust bearing structure).

(2) In the slide device of the present invention, it is preferable that silicon oxide be oxide of silicon derived from silicon which the above-mentioned slide member contains; such slide member being made of a silicon-containing material.

Due to such a constitution, a bonding force between the slide member made of a silicon-containing material and the hydrate of silicon oxide can be increased and thereby it is possible to suppress the removal of the hydrate of silicon oxide from a surface of the slide member made of a silicon-containing material.

(3) In the slide device of the present invention, it is preferable that the slide member made of a silicon-containing material be subjected to treatment for forming the hydrate of silicon oxide on the slide surface before the slide member made of a silicon-containing material is incorporated into the slide device.

Due to such a constitution, the hydrate of silicon oxide can be formed with the higher degree of freedom in determining steps of treatment and under a condition (for example, a pressure condition or a temperature condition) where a larger efficiency or more advantageous effects can be acquired compared to a case where the hydrate of silicon oxide is formed on the slide surface after the slide member made of a silicon-containing material is incorporated into the slide device.

(4) In the slide device of the present invention, it is preferable that the treatment for forming the hydrate of silicon oxide on the slide surface be running-in treatment.

"Running-in treatment" is treatment where a friction is imparted to a slide surface by gradually increasing a load in accordance with predetermined steps. In the present invention, a friction is imparted to the slide surface until a change rate of a frictional coefficient reaches a predetermined value (for example, 5%) or less at a fixed load and, thereafter, the load is increased in step with a predetermined value (for example, 50N) for each step (see FIG. 4 described later). Running-in treatment is performed in water, for example. A maximum load imparted during running-in treatment (hereinafter referred to as the maximum load) is preferably larger than a load applied when the slide device is actually used, and is more preferably 10 times larger than the load.

Here, it has been known that by applying running-in treatment to a member made of a material which contains silicon, a reaction referred to as "tribochemical reaction" occurs so that hydrate of silicon oxide is formed on a slide surface (see, for example, Tagami, Hiroo (1989), Special Feature, "Tribology of Ceramics", Tribologist, Vol. 34, No 2, 140 (in Japanese)).

The inventors of the present invention have found out that a slide surface of a slide member made of a silicon-containing material to which running-in treatment is applied not only simply exhibits a low frictional force but also further increases hydrophilicity on the slide surface of the slide member made of a silicon-containing material due to a large surface free energy thus making the blood component adhere only with greater difficulty to the slide surface.

In view of the above, according to the slide device of the present invention described in (4), when the slide device is used in an aqueous liquid containing a blood component, a frictional force can be much reduced compared to a conventional slide device.

(5) In the slide device of the present invention, it is preferable that one of the fixed-side slide member and the rotary-side slide member be formed of a slide member made of silicon carbide as a slide member made of a silicon-containing material, and the other of the fixed-side slide member and the rotary-side slide member be formed of a slide member made of carbon.

Silicon carbide is a material which has excellent hardness and durability and also is suitable for running-in treatment. Carbon is a soft material which is suitable for being used with silicon carbide. Accordingly, according to the slide device described in the above-mentioned (5), the present invention is applicable to the commonly used combinations of slide members.

(6) In the slide device of the present invention, it is preferable that the slide member made of carbon be formed of a slide member made of carbon to which running-in treatment is not applied.

It is found that when running-in treatment is applied to the slide member made of carbon, a tribochemical reaction does not occur and surface free energy is lowered (see experimental example 1 described later, particularly FIG. 6B). That is, with respect to the slide member made of carbon to which running-in treatment is applied, the hydrophilicity of the slide surface is lowered. In view of the above, according to the slide device described in the above-mentioned (6), compared to a case where a slide member made of carbon to which running-in treatment is applied is used, it is possible to make the blood component adhere only with difficulty to a slide surface of the slide member made of carbon.

(7) In the slide device of the present invention, it is preferable that an average surface roughness of the slide surface of the slide member made of carbon falls within a range of 0.01 µm to 1.0 µm.

Due to such a constitution, it is possible to prevent the hydrophilicity of the slide surface from becoming excessively low and it is also possible to prevent a frictional force attributed to the roughness of the slide surface from becoming excessively large.

With respect to the slide member made of carbon, it is thought that the average surface roughness of the slide surface is relevant to the magnitude of the surface free energy (see the experimental example 1 described later).

The reason the average surface roughness of the slide surface of the slide member made of carbon preferably falls within a range of 0.01 μm to 1.0 μm is that when the average surface roughness is set smaller than 0.01 μm, there arises a case where the slide surface is so flat that the hydrophilicity of the slide surface becomes excessively low, while when the average surface roughness is set larger than 1.0 μm, there arises a case where the unevenness of the surface becomes excessively large so that a frictional force attributed to the roughness of the slide surface becomes excessively large.

From the above-mentioned viewpoints, the average surface roughness of the slide surface of the slide member made of carbon more preferably falls within a range of 0.05 μm to 0.50 μm, and still more preferably falls within a range of 0.10 μm to 0.25 μm.

(8) In the slide device of the present invention, it is preferable that the average surface roughness of the slide surface of the slide member made of silicon carbide be set smaller than the average surface roughness of the slide surface of the slide member which is made of carbon.

Due to such a constitution, it is possible to suppress the hydrophilicity of the slide surface of the slide member made of carbon from becoming excessively low so that it is possible to make the blood component adhere only with difficulty to the slide surface of the slide member made of carbon.

(9) In the slide device of the present invention, it is preferable that the fixed-side slide member and the rotary-side slide member, both being slide members made of a silicon-containing material, are formed of a slide member made of silicon carbide.

Due to such a constitution, both the slide surface of the fixed-side slide member and the slide surface of the rotary-side slide member have hydrate of silicon oxide and hence, it is possible to make the blood component adhere only with difficulty to both the slide surface with respect to both the fixed-side slide member and the rotary-side slide member. As a result, when the slide device is used in an aqueous liquid containing a blood component, a frictional force can be further reduced compared to a conventional slide device.

(10) In the slide device of the present invention, it is preferable that the slide device is a slide device which is used in an aqueous liquid containing a blood component in a state where the fixed-side slide member and the rotary-side slide member are brought into contact with each other.

The slide device of the present invention is suitably applicable to the above-mentioned slide device.

"A state where the slide surface of the fixed-side slide member and the slide surface of the rotary-side slide member are brought into contact with each other" means not only a state where the slide surfaces are completely brought into contact with each other but also a case where an extremely small gap exists between the slide surfaces and a liquid (for example, a cool sealing liquid, an aqueous liquid containing a blood component or the like) which intrudes the gap is present.

(11) In the slide device of the present invention, it is preferable that the slide device is a slide device which further includes an intermediate slide member which is positioned between the fixed-side slide member and the rotary-side slide member, and is used in an aqueous liquid containing a blood component in a state where the fixed-side slide member and the rotary-side slide member face each other in an opposed manner with the intermediate slide member interposed therebetween.

The slide device of the present invention is also suitably applicable to the above-mentioned slide device.

As the intermediate slide member, it is possible to use, for example, a member made of carbon, one selected from a group consisting of a variety of ceramics (for example, silicon carbide), one selected from a group consisting of a variety of plastics (for example, PTFE) or one selected from a group consisting of a variety of sintered hard alloys.

(12) The mechanical seal of the present invention includes the slide device described in any one of the above-mentioned (1) to (10).

According to the mechanical seal of the present invention, since the mechanical seal includes the slide device of the present invention which can further reduce a frictional force compared to a conventional slide device when the slide device is used in an aqueous liquid containing a blood component, the mechanical seal can acquire a stable sliding state and thereby the mechanical seal can acquire high sealing property.

(13) The pump of the present invention includes the mechanical seal of the present invention.

According to the pump of the present invention, the pump includes the mechanical seal provided with the slide device of the present invention and hence, the pump can acquire high sealing property, and can be operated stably even when a moving force is imparted to an aqueous liquid containing a blood component.

(14) It is preferable that the pump according to the present invention is an auxiliary artificial heart pump.

Due to such a constitution, the auxiliary artificial heart pump includes the mechanical seal provided with the slide device of the present invention and hence, it is possible to provide the auxiliary artificial heart pump which can be operated more stably compared to a conventional auxiliary artificial heart pump.

(15) The auxiliary artificial heart system of the present invention includes the auxiliary artificial heart pump of the present invention.

According to the auxiliary artificial heart system of the present invention, the system includes the auxiliary artificial heart pump of the present invention which can be operated more stably compared to a conventional auxiliary artificial heart pump and hence, it is possible to provide the highly reliable auxiliary artificial heart system.

The "auxiliary artificial heart system" means a system which includes a control device, an artificial blood tube and the like besides the auxiliary artificial heart pump and is provided for assisting a function of a heart of a man who wears the auxiliary artificial heart system.

(16) According to another aspect of the present invention, there is provided a rotary device which includes: a rotary shaft having a slide surface and a bearing member having a slide surface, the rotary device being used in an aqueous liquid containing a blood component in a state where the rotary shaft is inserted into the bearing member, wherein at least one of the rotary shaft and the bearing member is formed of "a member which is made of a material containing silicon and has hydrate of silicon oxide on the slide surface thereof (hereinafter referred to as a slide member made of a silicon-containing material)".

According to the rotary device of the present invention, at least one of the rotary shaft and the bearing member is formed of the slide member made of a silicon-containing material and hence, in the same manner as the slide device of (1), "hydrate of silicon oxide which has high hydrophilicity" is formed on the slide surface. Accordingly, "a blood component having hydrophobicity in general" hardly adheres to the slide surface and thereby when the rotary device is used in an aqueous liquid containing a blood component, the rotary device can reduce a frictional force more compared to a conventional rotary device.

The above-mentioned rotary device may be a rotary device which has the so-called radial bearing structure.

According to the present invention, the blood from which the blood component is derived is not limited to human blood, and may be the blood of various kinds of animals such as a mammal, a bird, a reptile or the like besides human blood.

(17) The pump of the present invention includes the rotary device of the present invention.

According to the pump of the present invention, the pump includes the rotary device of the present invention and hence, the pump can be operated stably even when the pump is used in an aqueous liquid containing a blood component.

(18) It is preferable that the pump according to the present invention is an auxiliary artificial heart pump.

Due to such a constitution, the auxiliary artificial heart pump includes the rotary device of the present invention and hence, it is possible to provide the auxiliary artificial heart pump which can be operated more stably compared to a conventional auxiliary artificial heart pump.

(19) The auxiliary artificial heart system of the present invention includes the auxiliary artificial heart pump of the present invention.

According to the auxiliary artificial heart system of the present invention, the system includes the auxiliary artificial heart pump of the present invention which can be operated more stably compared to a conventional auxiliary artificial heart pump and hence, it is possible to provide the highly reliable auxiliary artificial heart system.

BRIEF DESCRIPTIONS OF THE DRAWINGS

FIG. 10 is a graph showing a change in frictional coefficient in a slide device according to an experimental example 3.

BEST MODE FOR CARRYING OUT THE INVENTION

Figure 1:
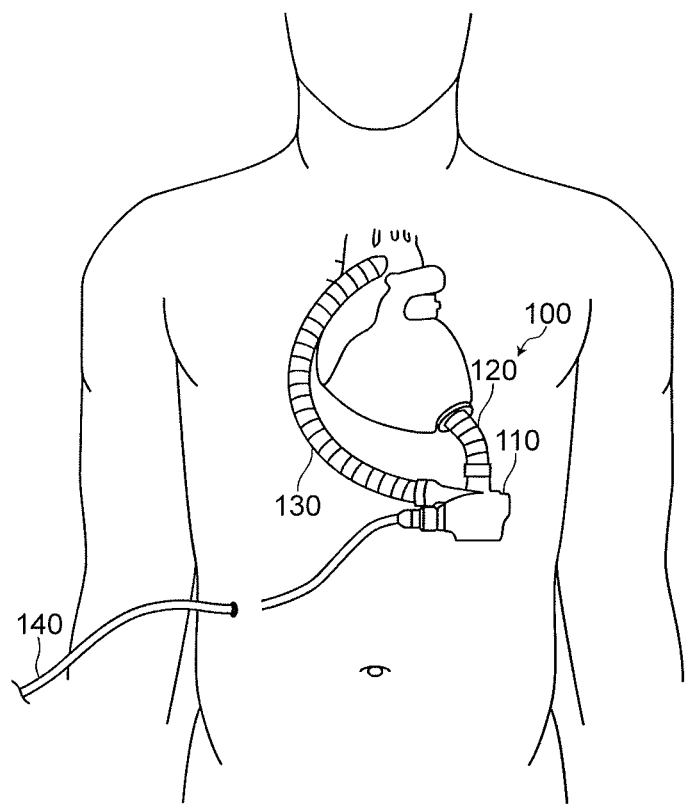
FIG. 1 is a view for explaining an auxiliary artificial heart system 100 according to an embodiment 1.

Hereinafter, a slide device, a rotary device, a pump and an auxiliary artificial heart system of the present invention are explained in conjunction with embodiments shown in the drawings.

[Embodiment 1]

FIG. 1 is a view for explaining an auxiliary artificial heart system 100 according to an embodiment 1.

Figure 2:
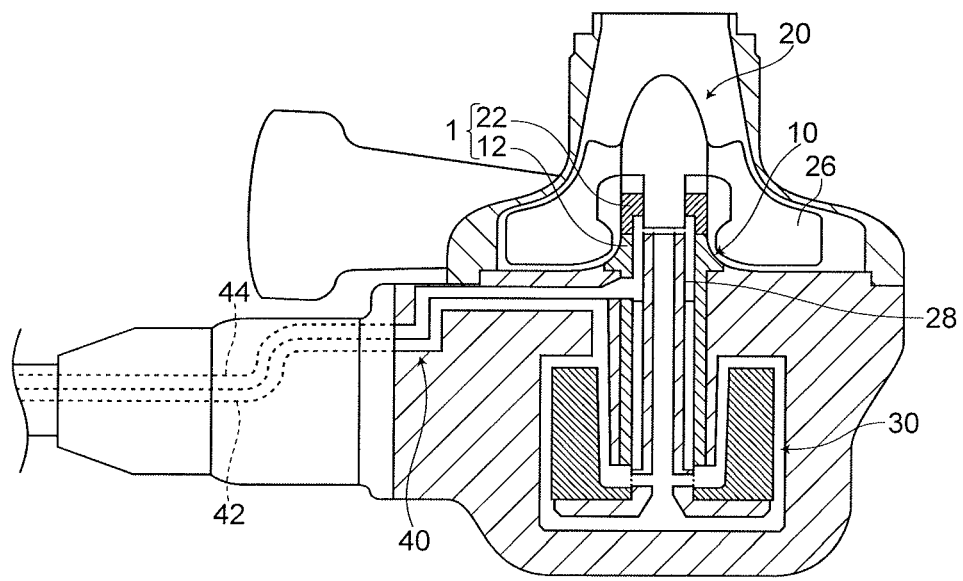
FIG. 2 is a cross-sectional view of an auxiliary artificial heart pump 110 according to the embodiment 1.

FIG. 2 is a cross-sectional view of an auxiliary artificial heart pump 110 according to the embodiment 1.

Figure 3A:
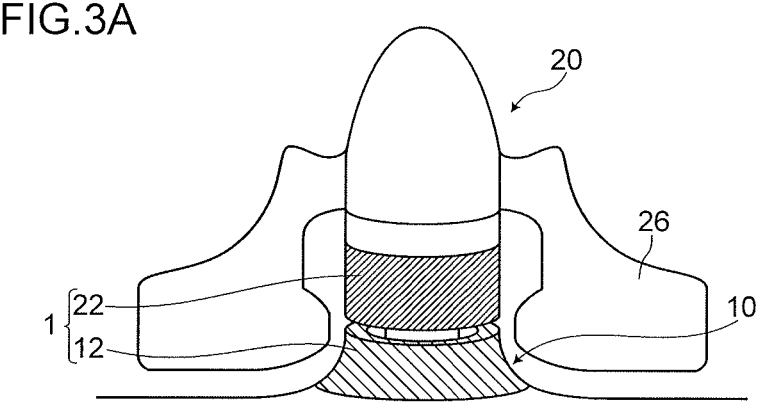
FIG. 3A to FIG. 3C are views for explaining a slide device 1 according to the embodiment 1.
Figure 3B:
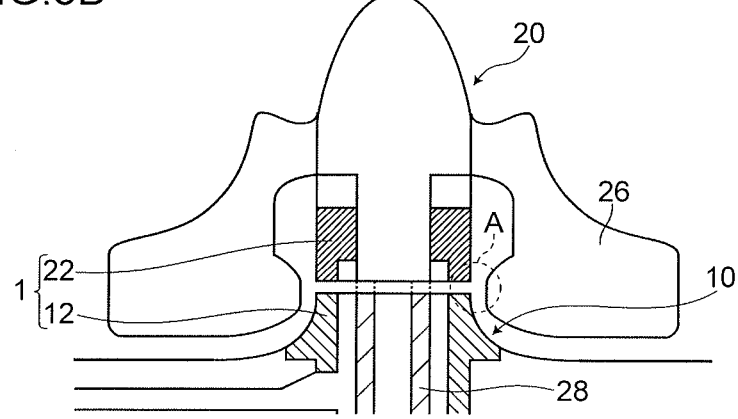
Figure 3C:
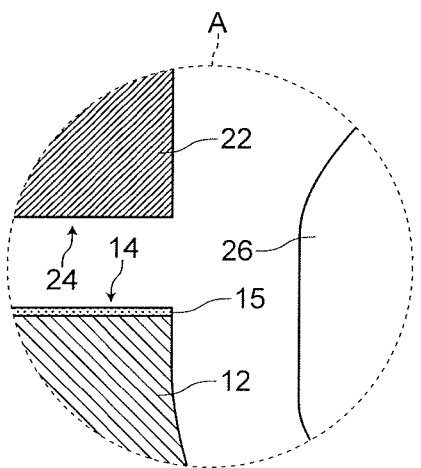

FIG. 3A to FIG. 3C are views for explaining a slide device 1 according to the embodiment 1, wherein FIG. 3A is a perspective view of a portion including the slide device 1, FIG. 3B is a cross-sectional view of the portion including the slide device 1, and FIG. 3C is an enlarged view of a portion indicated by symbol A in FIG. 3B. In FIG. 3A to FIG. 3C, for facilitating the understanding of the explanation, a fixed-side slide member 12 and a rotary-side slide member 22 are shown in a separated manner.

Figure 4A:
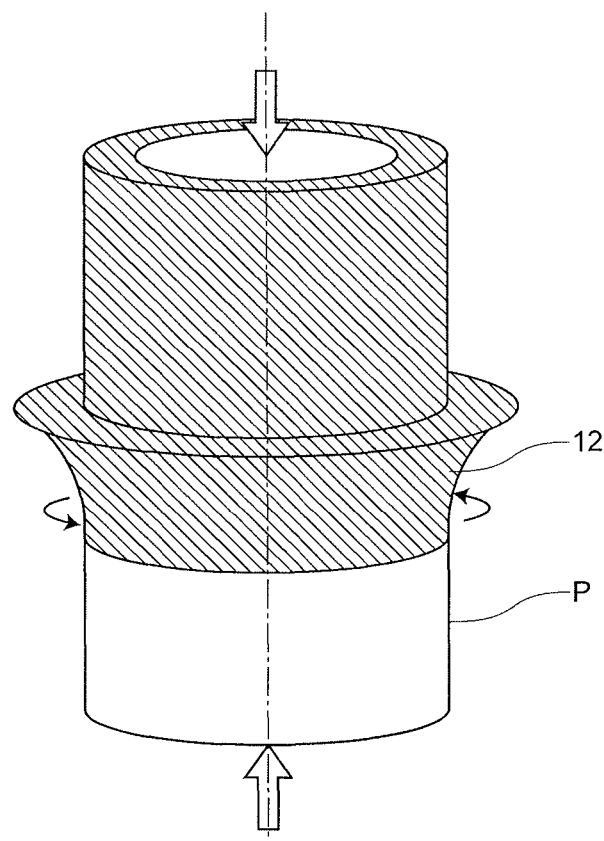
FIG. 4A and FIG. 4B are views for explaining running-in treatment in the embodiment 1.
Figure 4B:
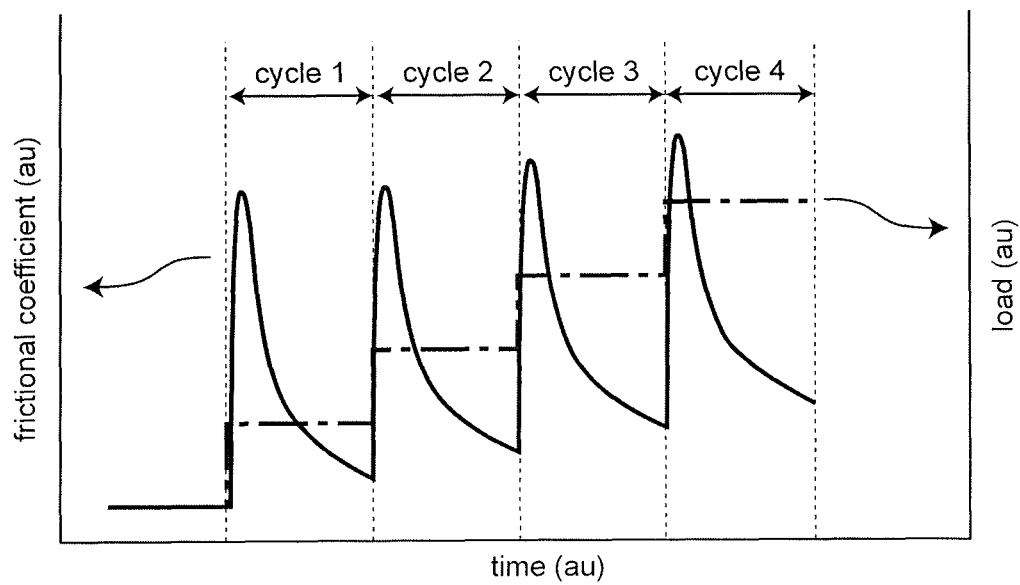

FIG. 4A and FIG. 4B are views for explaining running-in treatment in the embodiment 1, wherein FIG. 4A is a schematic view for explaining running-in treatment, and FIG. 4B is a graph showing the relationship between a load, a frictional coefficient and a time in running-in treatment. An arrow in FIG. 4A indicates a state where a load is applied to the slide device 1. In FIG. 4B, a frictional coefficient and a load are taken on an axis of abscissas, wherein both the frictional coefficient and the load are increased as the axis of ordinates extends upwardly.

The auxiliary artificial heart system 100 according to the embodiment 1 includes, as shown in FIG. 1, an auxiliary artificial heart pump 110, artificial blood vessels 120, 130 and a control device 150 (not shown in the drawing). Here, the control device 150 is provided outside the body of a user of the auxiliary artificial heart system 100, and is connected to the auxiliary artificial heart pump 110 through a cable 140.

The auxiliary artificial heart pump 110 is a blood pump for assisting a function of a left ventricle of a heart, and is embedded in the inside of a human body. As shown in FIG. 2, the auxiliary artificial heart pump 110 is a pump including a fixed part 10, a rotary part 20, a drive part 30 and a cool sealing liquid circulating part 40.

The fixed part 10 includes a fixed-side slide member 12 (so-called seat ring).

The fixed-side slide member 12 has, as shown in FIG. 3C, a slide surface 14.

The rotary part 20 includes a rotary-side slide member 22 (so-called seal ring), an impeller 26 and a rotary shaft 28.

The rotary-side slide member 22 has a slide surface 24.

The impeller 26 applies a moving force to blood.

The rotary shaft 28 is connected with the drive part 30, and rotates the whole rotary part 20 when a driving force (rotational force) is imparted from the drive part 30.

The fixed-side slide member 12 and the rotary-side slide member 22 constitute the slide device 1 according to the embodiment 1. The slide device 1 is explained in detail later.

In the embodiment 1, the slide device 1 functions as a mechanical seal by itself.

The drive part 30 rotates the rotary part 20 by way of the rotary shaft 28. The drive part 30 includes a rotary motor, for example.

The cool sealing liquid circulating part 40 allows a cool sealing liquid (for example, water or physiological salt solution) which has a function of lubricating and cooling the inside of the auxiliary artificial heart pump 110, a function of maintaining the sealing property of the cool sealing liquid and the like to pass through the inside of the auxiliary artificial heart pump 110 from a cool sealing liquid inlet port 42, and discharges the cool sealing liquid from a cool sealing liquid outlet port 44. The cool sealing liquid also has a function of performing lubrication and cooling between the rotary shaft 28 and the fixed part 10. Further, the cool sealing liquid has a function of suppressing the intrusion of a blood component through a gap defined between the fixed-side slide member 12 and the rotary-side slide member 22 (ensuring the sealing property), and a function of cleaning the slide surfaces.

Hereinafter, the slide device 1 according to the embodiment 1 is explained in detail.

As shown in FIG. 3A to FIG. 3C, the slide device 1 according to the embodiment 1 is a slide device which includes the fixed-side slide member 12 having the slide surface 14 and the rotary-side slide member 22 having the slide surface 24, and is used in an aqueous liquid containing a blood component (blood in the embodiment 1) in a state where the fixed-side slide member 12 and the rotary-side slide member 22 are brought into contact with each other.

The slide device 1 is a slide device which is used in a state where a predetermined load is applied between the fixed-side slide member 12 and the rotary-side slide member 22 in the direction along a rotation axis of the rotary-side slide member 22 (a slide device having the so-called thrust bearing structure). A predetermined load can be applied by making use of a repulsive force generated between magnets, for example.

In the slide device 1, a gap of 1 μm or less formed between the fixed-side slide member 12 and the rotary-side slide member 22 in a use state and hence, blood and cool sealing liquid enter the gap. Out of components of blood and the cool sealing liquid, a water component lubricates the slide surfaces. Further, as described previously, the cool sealing liquid lubricates the slide surfaces.

The fixed-side slide member 12 is formed of a slide member made of a silicon-containing material. That is, the fixed-side slide member 12 is formed of a member which is made of a material containing silicon and has hydrate 15 made of silicon oxide on its slide surface 14 (see FIG. 3C). To be more specific, the fixed-side slide member 12 is formed of a slide member made of silicon carbide.

Silicon oxide from which the hydrate 15 of silicon oxide is formed is oxide of silicon derived from silicon which the slide member made of a silicon-containing material (the fixed-side slide member 12) contains.

The slide member made of a silicon-containing material (the fixed-side slide member 12) is the member to which running-in treatment which is treatment for forming the hydrate 15 of silicon oxide on the slide surface 14 is applied before the slide member made of a silicon-containing material (the fixed-side slide member 12) is assembled as a part of the slide device 1.

Running-in treatment performed in the embodiment 1 is explained in conjunction with FIG. 4. First, as shown in FIG. 4A, the slide surface 14 of the fixed-side slide member 12 is abutted on a surface of an opposedly facing member P. Then, the fixed-side slide member 12 and the opposedly facing member P are slid on each other in water in a state where a load is applied to the fixed-side slide member 12 in the axial direction. By continuing such a sliding operation for some time, slide surfaces of both members acquire affinity therebetween between so that a frictional coefficient between the members is lowered (see step 1 in FIG. 4B).

When a frictional coefficient between members is lowered to some extent and a change in the frictional coefficient with time becomes small, the fixed-side slide member 12 and the opposedly facing member P are further slid on each other in water while applying a larger load to the fixed-side slide member 12. This operation is repeated until the slide surface 14 of the fixed-side slide member 12 assumes a desirable state (see step 2 and steps which succeed step 2 in FIG. 4B).

A tribochemical reaction is generated in the above-mentioned running-in treatment so that the hydrate 15 of silicon oxide is formed on the slide surface 14 of the fixed-side slide member 12.

Running-in treatment can be performed, for example, under a condition where a load is increased by 50N each time, a change in a frictional coefficient with time at a fixed load decreases (for example, a reduction rate of the frictional coefficient within the fixed period being 5% or less), and this operation is repeated 4 times. At a point of time that the operation is repeated 4 times, the load becomes the maximum load of 200N.

The average surface roughness of the slide surface 14 of the slide member made of silicon carbide (the fixed-side slide member 12) is smaller than the average surface roughness of the slide surface 24 of the slide member made of carbon (the rotary-side slide member 22) described later, and is set to 0.05 μm, for example.

The rotary-side slide member 22 is formed of the slide member made of carbon to which running-in treatment is not applied. The average surface roughness of the slide surface 24 of the slide member made of carbon (the rotary-side slide member 22) falls within a range of 0.01 μm to 1.0 μm, more preferably falls within a range of 0.05 μm to 0.5 μm, and still more preferably falls within a range of 0.10 μm to 0.25 μm. For example, the average surface roughness of the slide surface 24 is set to 0.15 μm.

Next, advantageous effects obtained by the slide device 1, the pump (auxiliary artificial heart pump 110) and the auxiliary artificial heart system 100 according to the embodiment 1 are explained.

According to the slide device 1 of the embodiment 1, at least one of the fixed-side slide member and the rotary-side slide member (the fixed-side slide member 12) is formed of a slide member made of a silicon-containing material and hence, "hydrate of silicon oxide having high hydrophilicity" is formed on the slide surface. Accordingly, "a blood component having hydrophobicity in general" hardly adheres to the slide surface. As a result, the slide device 1 according to the embodiment 1 can decrease a frictional force when the slide device 1 is used in an aqueous liquid containing a blood component compared to a conventional slide device.

According to the slide device 1 of the embodiment 1, silicon oxide is oxide of "silicon derived from silicon which the slide member made of a silicon-containing material contains". Accordingly, a bonding strength of the slide member made of a silicon-containing material and hydrate of silicon oxide can be increased. As a result, it is possible to suppress the removal of the hydrate of silicon oxide from the surface of the slide member made of a silicon-containing material.

According to the slide device 1 of the embodiment 1, treatment for forming the hydrate 15 of silicon oxide on the slide surface 14 is applied before the slide member made of a silicon-containing material 12) is assembled as a part of the slide device 1. Accordingly, hydrate of silicon oxide can be formed under a condition (for example, a pressure condition or a temperature condition) with the higher degree of freedom and higher effects compared to a case where hydrate of silicon oxide is formed on the slide surface after the slide member made of a silicon-containing material is assembled as a part of the slide member.

According to the slide device 1 of the embodiment 1, treatment for forming the hydrate 15 of silicon oxide on the slide surface 14 is "running-in treatment" and hence, when the slide device 1 is used in an aqueous liquid containing a blood component, a frictional force can be further decreased compared to a conventional slide device.

According to the slide device 1 of the embodiment 1, one of the fixed-side slide member and the rotary-side slide member (the fixed-side slide member 12) is formed of a slide member made of silicon carbide, and the other of the fixed-side slide member and the rotary-side slide member (the rotary-side slide member 22) is formed of a slide member made of carbon. Accordingly, the present invention is applicable to a slide device having the general combination of the slide members.

According to the slide device 1 of the embodiment 1, the slide member made of carbon is formed of "the slide member made of carbon to which running-in treatment is not applied" and hence, the adhesion of a blood component to the slide surface of the slide member made of carbon can be suppressed more compared to a case where the slide member made of carbon to which running-in treatment is applied is used.

According to the slide device 1 of the embodiment 1, the average surface roughness of the slide surface of the slide member made of carbon falls within a range of 0.01 μm to 1.0 μm and hence, the excessive lowering of hydrophilicity of the slide surface can be prevented, and the excessive increase of a frictional force attributed to a roughness of the slide surface can be also prevented.

Further, according to the slide device 1 of the embodiment 1, the average surface roughness of the slide surface of the slide member made of silicon carbide is smaller than the average surface roughness of the slide surface of the slide member made of carbon. Accordingly, the excessive lowering of hydrophilicity of the slide surface of the slide member made of carbon can be suppressed and hence, a blood component adheres only with more difficulty to the slide surface of the slide member made of carbon.

The mechanical seal according to the embodiment 1 includes the slide device 1 of the embodiment 1. Accordingly, when the mechanical seal is used in an aqueous liquid containing a blood component, the mechanical seal which includes the slide device of this embodiment can decrease a frictional force compared to a conventional slide device and hence, the mechanical seal can acquire a stable sliding state thus acquiring high sealing property.

The pump according to the embodiment 1 includes the mechanical seal according to the embodiment 1. Accordingly, the pump can acquire high sealing property so that the pump can be stably operated even when a moving force is applied to an aqueous liquid containing a blood component.

Further, the pump according to the embodiment 1 is the auxiliary artificial heart pump 110 which includes the mechanical seal having the slide device 1 according to the embodiment 1. Accordingly, it is possible to provide the auxiliary artificial heart pump which can be operated more stably than a conventional auxiliary artificial heart pump.

The auxiliary artificial heart system 100 according to the embodiment 1 includes the auxiliary artificial heart pump 110 according to the embodiment 1 which can be operated more stably than a conventional auxiliary artificial heart pump. Accordingly, it is possible to provide the highly reliable auxiliary artificial heart system 100.

The slide device 1 according to the embodiment 1 is the slide device which is used in a state where a predetermined load is applied between the fixed-side slide member 12 and the rotary-side slide member 22 in the direction along a rotation axis of the rotary-side slide member 22. The present invention is preferably applicable to the slide device having such structure (so-called thrust bearing structure).

The slide device 1 according to the embodiment 1 is a slide device which is used in an aqueous liquid containing a blood component in a state where the fixed-side slide member 12 and the rotary-side slide member 22 are brought into contact with each other. The present invention is preferably applicable to the slide device having such a constitution.

[Embodiment 2]

Figure 5A:
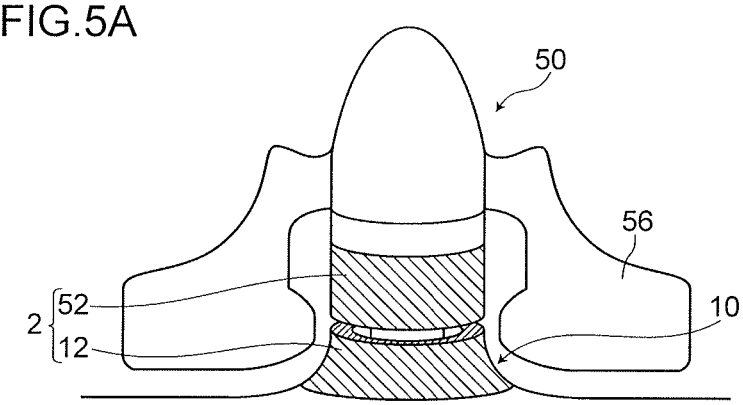
FIG. 5 is a view for explaining a slide device 2 according to an embodiment 2.
Figure 5B:
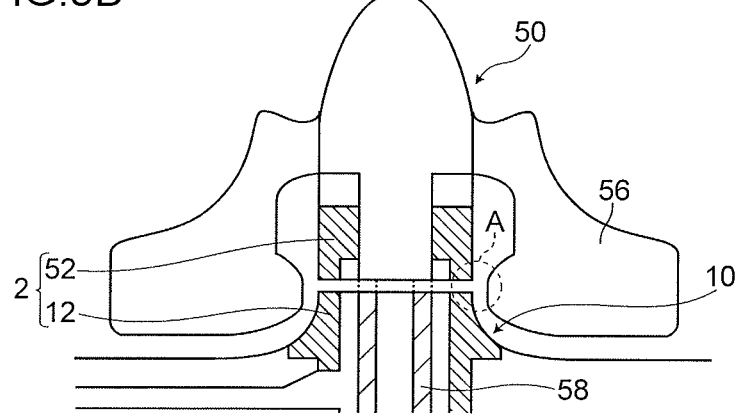
Figure 5C:
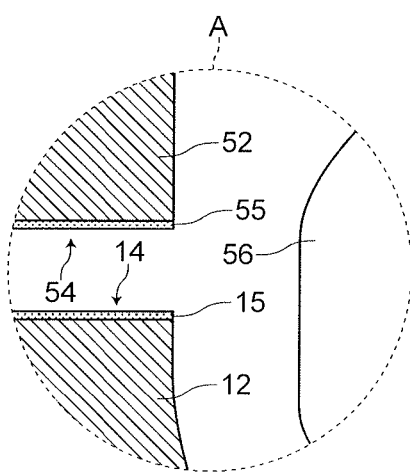

FIG. 5A to FIG. 5C are views for explaining a slide device 2 according to an embodiment 2. FIG. 5A is a perspective view of a portion including the slide device 2, FIG. 5B is a cross-sectional view of the portion including the slide device 2, and FIG. 5C is an enlarged view showing a portion indicated by a symbol A in FIG. 5B. Here, in FIG. 5A to FIG. 5C, for facilitating the understanding of the explanation, a fixed-side slide member 12 and a rotary-side slide member 52 are shown in a separated manner.

Although the slide device 2 according to the embodiment 2 basically has the substantially same constitution as the slide device 1 according to the embodiment 1, the slide device 2 according to the embodiment 2 differs from the slide device 1 according to the embodiment 1 with respect to the constitution of the rotary-side slide member. That is, as shown in FIG. 5A to FIG. 5C, in the slide device 2 according to the embodiment 2, the rotary-side slide member 52 is formed of a slide member made of silicon carbide and has hydrate 55 of silicon oxide on a slide surface 54. That is, in the slide device 2 according to the embodiment 2, both the fixed-side slide member 12 and the rotary-side slide member 52 are formed of a slide member made of silicon carbide.

Although the slide device 2 according to the embodiment 2 differs from the slide device 1 according to the embodiment 1 with respect to the constitution of the rotary-side slide member, both the fixed-side slide member 12 and the rotary-side slide member 52 are formed of a slide member made of silicon carbide. Accordingly, both a slide surface 14 of the fixed-side slide member 12 and the slide surface 54 of the rotary-side slide member 52 have hydrate 15, 55 of silicon oxide respectively. Due to such a constitution, according to the slide device 2 of the embodiment 2, a blood component hardly adheres to both the fixed-side slide member and the rotary-side slide member. Accordingly, when the slide device 2 is used in an aqueous liquid containing a blood component, a frictional force can be decreased more compared to the slide device 1 according to the embodiment 1.

The slide device 2 according to the embodiment 2 has the substantially same constitution as the slide device 1 according to the embodiment 1 with respect to the constitutions other than the constitution of the rotary-side slide member and hence, the slide device 2 according to the embodiment 2 can acquire advantageous effects corresponding to such constitutions out of advantageous effects acquired by the slide device 1 of the embodiment 1.

EXPERIMENTAL EXAMPLE 1

Figure 6A:
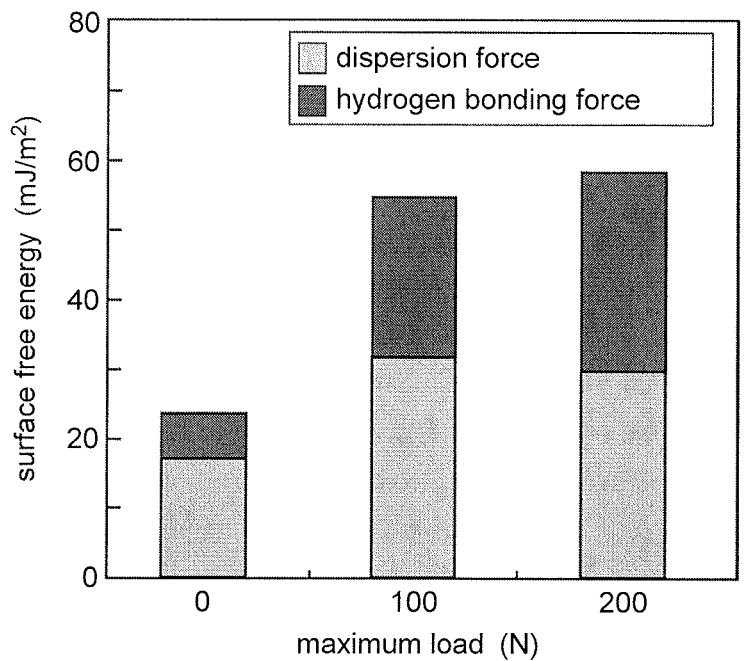
FIG. 6 is a bar graph for explaining a change in surface free energy in an experimental example 1.
Figure 6B:
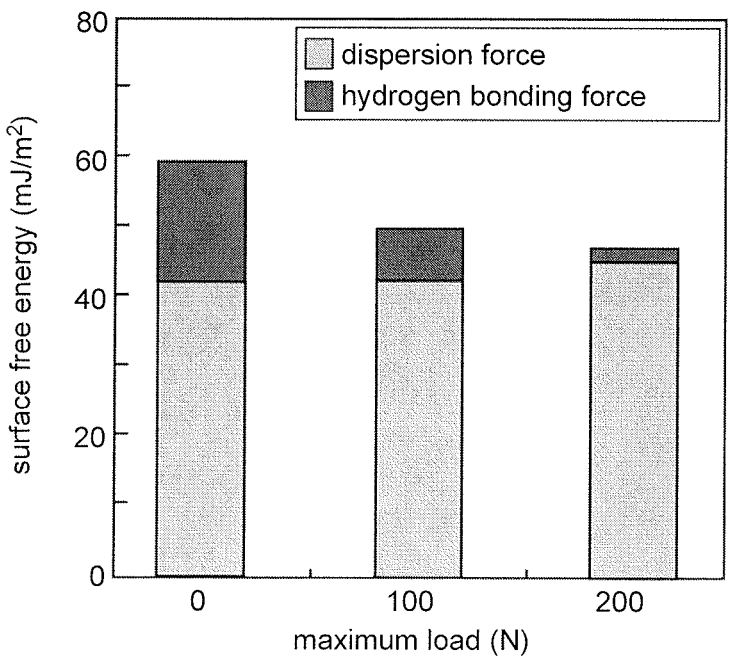

FIG. 6A and FIG. 6B are bar graphs for explaining a change in surface free energy in the experimental example 1. FIG. 6A is a bar graph relating to silicon carbide, and FIG. 6B is a bar graph relating to carbon. In FIG. 6A and FIG. 6B, with respect to the surface free energy, a portion of the energy generated by a dispersion force is indicated by light gray color, and a portion of the energy generated by a hydrogen bonding force is indicated by dark gray color.

In the experimental example 1, the difference in surface free energy among cases where a maximum load in running-in treatment differs from each other is measured using a member made of silicon carbide or carbon.

Although an running-in treatment method is substantially equal to the running-in treatment method described in the embodiment 1 so that their repeated explanation is omitted, the maximum load is set to 0N (that is, no running-in treatment being performed), 100N and 200N respectively. Here, with respect to the average surface roughness of the slide surface in an initial state, the average surface roughness of a member made of silicon carbide is 0.027 μm, and the average surface roughness of the member made of carbon is 0.258 μm. With respect to porosity, the member made of silicon carbide having porosity of 28.8% and the member made of carbon having porosity of 36.3% are used.

Here, the surface free energy can be roughly correlated with a magnitude of surface wettability, and it is thought that the larger the surface free energy, the higher hydrophilicity becomes.

As a method of measuring surface free energy, a method used commonly is adopted. Although the detailed explanation of the method is omitted, first, a surface tension to water and a surface tension to methylene iodide are measured by a contact angle measuring instrument (so-called liquid dropping method) and, then, surface free energy is calculated based on known data relating to water and methylene iodide by a formula.

As a result, first, as shown in FIG. 6A, with respect to the member made of silicon carbide, it is found that the larger the maximum load, the larger the surface free energy becomes. The reason for this is thought that hydrate of silicon oxide is formed on a slide surface due to a tribochemical reaction so that a hydrogen bonding force is significantly increased.

Next, as shown in FIG. 6B, with respect to the member made of carbon, it is found that the larger the maximum load, the smaller the surface free energy becomes. The reason for this is thought that the slide surface is leveled so that a hydrogen bonding force is decreased (carbon per se being a substance having strong hydrophobicity).

There is no substantial difference between being the fixed-side member and being the rotary-side member and hence, it is thought that the substantially same effect can be obtained even when a material of the fixed-side member and a material of the rotary side member is exchanged from each other.

As described above, with respect to the case where one of the fixed-side slide member and the rotary-side slide member is formed of a slide member made of silicon carbide and the other of the fixed-side slide member and the rotary-side slide member is formed of a slide member made of carbon, from a viewpoint of enhancing hydrophilicity of the slide surface thus suppressing the adhesion of a blood component to the slide surface, it is confirmed that it is preferable to use a slide member made of silicon carbide (a slide member made of a silicon-containing material) to which running-in treatment is applied as the slide member made of silicon carbide, and to use a slide member made of carbon to which running-in treatment is not applied as the slide member made of carbon.

EXPERIMENTAL EXAMPLE 2

Figure 7:
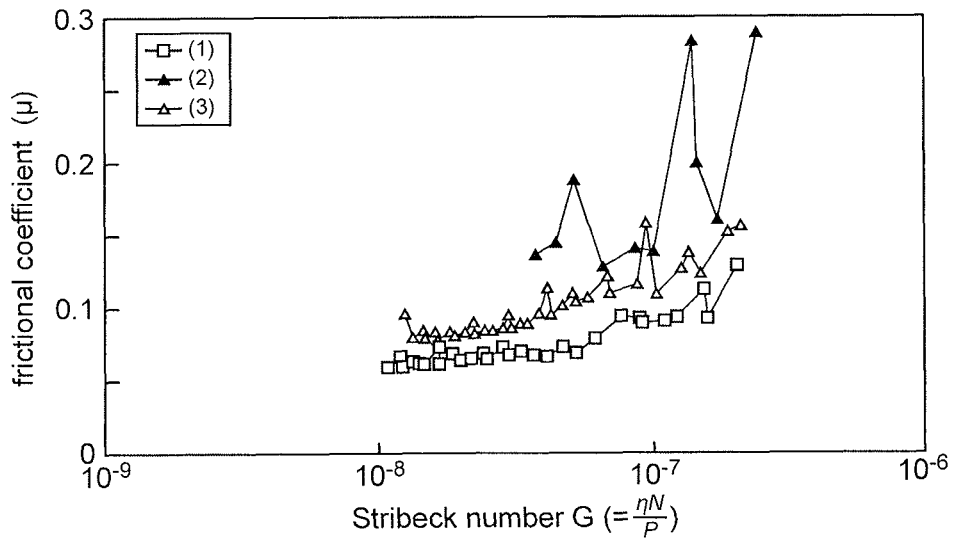
FIG. 7 is a graph of Stribeck curves in an experimental example 2.
Figure 8:
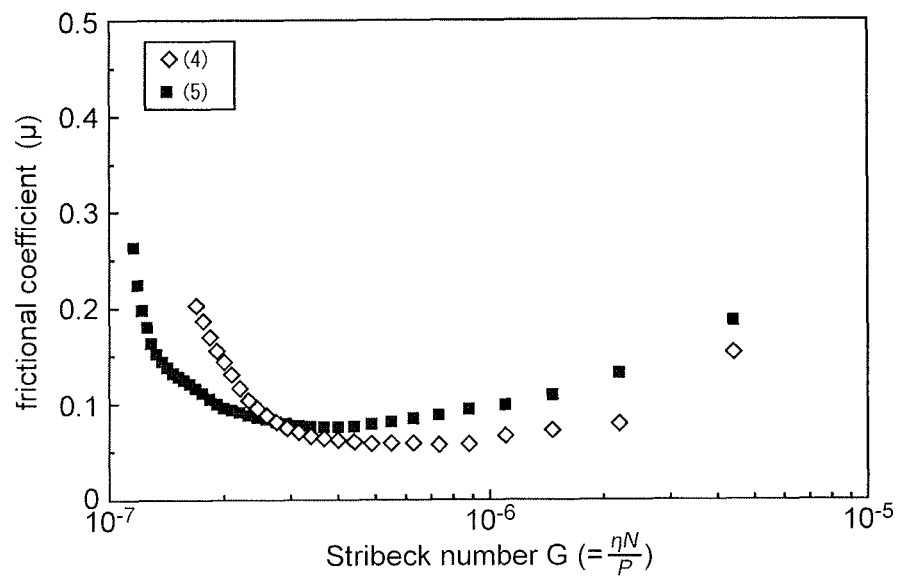
FIG. 8 is a graph of Stribeck curves in the experimental example 2.

FIG. 7 and FIG. 8 are graphs showing Stribeck curves in an experimental example 2.

In the experimental example 2, Stribeck curves are formed by assuming a case where one of the fixed-side slide member and the rotary-side slide member is formed of a slide member made of silicon carbide and the other of the fixed-side slide member and the rotary-side slide member is formed of a slide member made of carbon, and a case where both the fixed-side slide member and the rotary-side slide member are formed of a slide member made of silicon carbide.

In this specification, the Stribeck curves are curves which are drawn in a graph by taking a frictional coefficient μ on an axis of ordinates and a value obtained by dividing the product of viscosity and a shaft rotational speed by a load (hereinafter, referred to as Stribeck number) on an axis of abscissas.

Although not shown in the drawing, the test is performed in such a manner that a disc member corresponding to the fixed-side slide member and a ring member corresponding to the rotary-side slide member are prepared, the ring member is rotated in a state where the disc member and the ring member are brought into contact with each other, and a frictional torque is measured. Further, the disc member and the ring member are brought into an immersed state in a liquid for experiment, and a load applied between the disc member and the ring member is changed by applying a load to the disc member using an oil pressure.

An outer diameter of the prepared disc member and an outer diameter of the ring member are set to 20 mm respectively. A diameter of a hole formed in the ring member is set to 10 mm. With respect to the average surface roughness of a slide surface in an initial state, the average surface roughness of the slide surface of the member made of silicon carbide is 0.027 μm, and the average surface roughness of the slide surface of the member made of carbon is 0.258 μm. With respect to porosity, the member made of silicon carbide having porosity of 28.8% and the member made of carbon having porosity of 36.3% are used.

The measurement is carried out under conditions where a rotational speed of the rotary-side slide member is set to 800 rpm, a water temperature (a temperature of the liquid for experiment) is set to 18° C. to 20° C., and a load is set to 50N to 200N (212.3 kPa to 849.3 kpa in terms of a contact face pressure). As a liquid for experiment, water containing 15 vol % of blood plasma is used.

In the experimental example 2, Stribeck curves are formed with respect to the following cases (1) to (5). The cases (1) and (4) relate to the slide devices according to the present invention, and the cases (2), (3) and (5) relate to slide devices according to comparison examples. The results of the cases (1) to (3) are collectively shown in FIG. 7, and the results of the cases (4) and (5) are collectively shown in FIG. 8.

(1) The case where the disc member is formed of a slide member made of silicon carbide to which running-in treatment is applied, and the ring member is formed of a slide member made of carbon to which running-in treatment is not applied (indicated by a blanked quadrangle).

(2) The case where the disc member is formed of a slide member made of silicon carbide to which running-in treatment is not applied, and the ring member is formed of a slide member made of carbon to which running-in treatment is not applied (indicated by a black matted triangle).

(3) The case where the disc member is formed of a slide member made of silicon carbide to which running-in treatment is applied, and the ring member is formed of a slide member made of carbon to which running-in treatment is applied (indicated by a blanked triangle).

(4) The case where the disc member is formed of a slide member made of silicon carbide to which running-in treatment is applied, and the ring member is also formed of the slide member made of silicon carbide to which running-in treatment is applied (indicated by a blanked rhombus).

(5) The case where the disc member is formed of a slide member made of silicon carbide to which running-in treatment is not applied, and the ring member is also formed of a slide member made of silicon carbide to which running-in treatment is not applied (indicated by a black matted quadrangle).

As a result, in the case where the disc member is made of silicon carbide and the ring member is made of carbon, it is found that a frictional coefficient of the slide member according to the present invention (case (1)) substantially becomes lower than frictional coefficients of other slide members (cases (2), (3)). Accordingly, it is confirmed that the slide device according to the present invention can decrease a frictional force more compared to the conventional slide device when these slide devices are used in an aqueous liquid containing a blood component (see FIG. 7).

On the other hand, also in the case where both the disc member and the ring member are made of silicon carbide, it is found that a frictional coefficient of the slide member according to the present invention (case (4)) substantially becomes lower than a frictional coefficient of another slide member (case (5)). Accordingly, it is confirmed that the slide device according to the present invention can decrease a frictional force more compared to a conventional slide device when these slide devices are used in an aqueous liquid containing a blood component (see FIG. 8). The comparison made in FIG. 8 is also the comparison on the presence or the non-presence of running-in treatment and hence, it is confirmed that a frictional coefficient can be decreased by running-in treatment.

EXPERIMENTAL EXAMPLE 3

Figure 9:
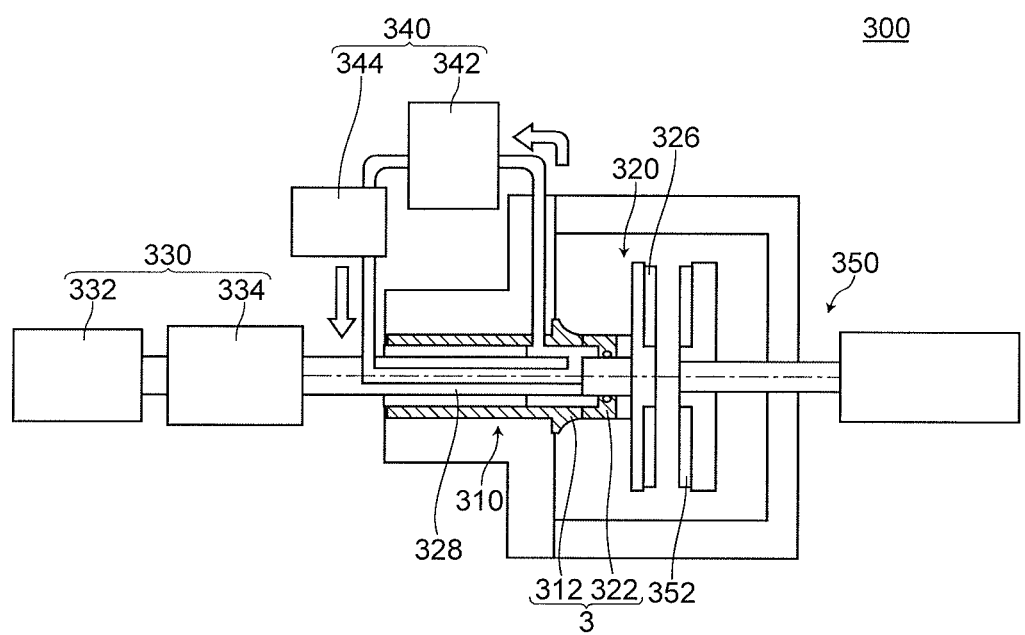
FIG. 9 is a schematic view of an experiment device 300 in the experimental example 2.
Figure 11:
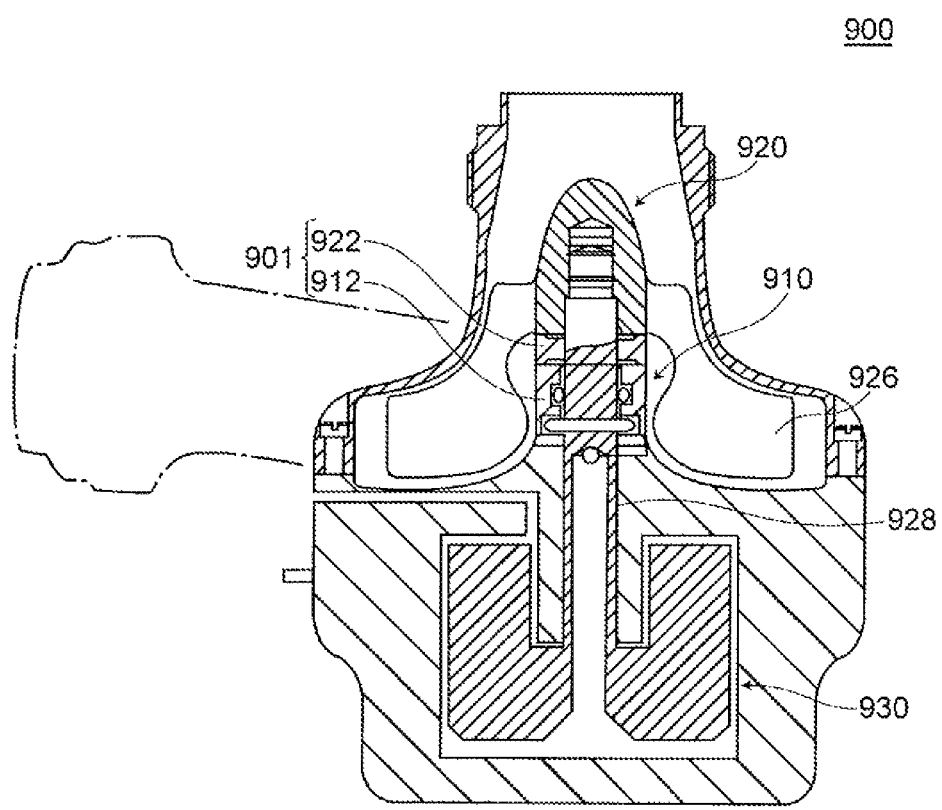
FIG. 11 is a cross-sectional view of a conventional auxiliary artificial heart pump 900.

FIG. 9 is a schematic view of an experiment device 300 used in an experimental example 3.

FIG. 10A to FIG. 10C are graphs for explaining a change in frictional coefficient of a slide device 3 according to the experimental example 3. FIG. 10A is a graph showing a result of a change in frictional coefficient with respect to the slide device 3 according to the experimental example 3, FIG. 10B is a graph showing a result of a change in frictional coefficient with respect to a slide device 3a according to a comparison example 1, and FIG. 10C is a graph showing a result of a change in frictional coefficient with respect to a slide device 3b according to a comparison example 2. In FIG. 10A to FIG. 10C, a frictional coefficient is taken on an axis of ordinates, and a time t (unit: minute) is taken on an axis of abscissas.

In the experimental example 3, a change in frictional coefficient with time is measured with respect to the case where both the fixed-side slide member and the rotary-side slide member are formed of a slide member made of silicon carbide.

The experimental example 3 is carried out using the experiment device 300 (see FIG. 9). The experiment device 300 substantially has the same structure as the auxiliary artificial heart pump 110 according to the embodiment 1. That is, the experiment device 300 includes a fixed part 310, a rotary part 320, a drive part 330 and a cool sealing liquid circulating part 340. Further, the experiment device 300 also includes a load adjusting part 350 for adjusting a load applied to a fixed-side slide member 312 and a rotary-side slide member 322 (described later).

The fixed part 310 includes the fixed-side slide member 312, and the fixed-side slide member 312 has a slide surface 314 (symbol not shown in the drawing).

The rotary part 320 includes the rotary-side slide member 322, a magnet 326 and a rotary shaft 328. The rotary-side slide member 322 has a slide surface 324 (symbol not shown in the drawing). The magnet 326 applies a load between the fixed-side slide member 312 and the rotary-side slide member 322 due to a repulsive force generated by the magnet 326 and a magnet 352 which is movable in the load adjusting part 350.

The drive part 330 includes a motor 332 and a torque detection part 334, and rotates the rotary part 320 by way of the rotary shaft 328.

The cool sealing liquid circulating part 340 includes a tank 342 and a pump 344, and generates the circulation of a cool sealing liquid.

The load adjusting part 350 includes the movable magnet 352. The movable magnet 352 is arranged such that the magnet 352 and the magnet 326 having the same polarity face each other in an opposed manner.

The slide device 3 used in the experimental example 3 is constituted of the fixed-side slide member 312 and the rotary-side slide member 322. The fixed-side slide member 312 and the rotary-side slide member 322 are exposed to a liquid for experiment, and the fixed-side slide member 312 and the rotary-side slide member 322 constitute a mechanical seal which prevents the intrusion of the liquid into the inside of the slide device 3.

Both the fixed-side slide member 312 and the rotary-side slide member 322 are formed of a slide member made of silicon carbide respectively.

Further, in the experimental example 3, to confirm advantageous effects of the slide device 3 according to the experimental example 3, an experiment is also carried out with respect to the comparison example 1 and the comparison example 2. Experiment devices used for the comparison example 1 and the comparison example 2 have substantially the same constitution as the experiment device 300 of the experimental example 3 except for that a fixed-side slide member and a rotary-side slide member of the comparison example 1 and the comparison example 2 differ from the fixed-side slide member and the rotary-side slide member of the experimental example 3 and hence, these experiment devices are not shown in the drawings and the detailed explanation of the constitutions of these comparison examples 1 and 2 is omitted.

In the comparison example 1, used is the slide device where the fixed-side slide member is formed of a slide member made of silicon carbide to which running-in treatment is not applied, and the rotary-side slide member is formed of a slide member made of carbon to which running-in treatment is not applied.

In the comparison example 2, used is the slide device where both the fixed-side slide member and the rotary-side slide member are formed of a slide member made of silicon carbide to which running-in treatment is not applied.

Experimental conditions are common among the experimental example 3, the comparison example 1 and the comparison example 2, wherein blood of a goat is used as an aqueous liquid containing a blood component, water is used as a cool sealing liquid, a rotational speed of the rotary part 320 is set to 2000 rpm, and a load applied to a slide surface is set to 2N.

As a result, with respect to the slide devices according to the comparison example 1 and the comparison example 2 having the constitution close to the constitution of a conventional slide device, a frictional coefficient is increased with a lapse of time so that the sliding becomes unstable (see FIG. 10B and FIG. 10C). To the contrary, with respect to the slide device 3 having the constitution of the present invention, neither the increase of a frictional coefficient nor the unstable sliding is found even when time elapses. Further, it is confirmed that a frictional coefficient per se is also remarkably decreased compared to the comparison examples (FIG. 10A).

[Embodiment 3]

A rotary device 4 (not shown in the drawing) according to the embodiment 3 is a rotary device which includes a rotary shaft having a slide surface and a bearing member having a slide surface, and is used in an aqueous liquid containing a blood component in a state where the rotary shaft is inserted into the bearing member, wherein at least one of the rotary member and the bearing member is a member which is made of a material containing silicon and has hydrate of silicon oxide on a slide surface thereof (hereinafter, referred to as a slide member made of silicon-containing material). That is, the rotary device 4 is a rotary device having the so-called radial bearing structure. In the present invention, both the rotary shaft and the bearing member are formed of a slide member made of silicon carbide.

A pump according to the embodiment 3 is a pump equipped with the rotary device 4, and is an auxiliary artificial heart pump. Further, an auxiliary artificial heart system according to the embodiment 3 is provided with the pump according to the embodiment 3.

In the rotary device 4 according to the embodiment 3, at least one of the rotary shaft and the bearing member is formed of a slide member made of a silicon-containing material. Accordingly, in the same manner as the slide device according to the embodiment 1, the slide member made of a silicon-containing material has hydrate of silicon oxide having high hydrophilicity on the slide surface thereof and hence, the adhesion of a blood component to the slide surface can be further effectively suppressed. As a result, when the rotary device 4 is used in an aqueous liquid containing a blood component, the rotary device 4 can decrease a frictional force more than the conventional rotary device.

The pump according to the embodiment 3 is provided with the rotary device 4 according to the embodiment 3. Accordingly, it is possible to provide a pump which can be operated stably even when a moving force is applied to an aqueous liquid containing a blood component.

Further, the pump according to the embodiment 3 is provided with the rotary device 4 according to the embodiment 3. Accordingly, it is possible to provide an auxiliary artificial heart pump which can be operated stably.

The auxiliary artificial heart system according to the embodiment 3 is provided with the auxiliary artificial heart pump according to the embodiment 3 which can be operated stably more than the conventional auxiliary artificial heart pump. Accordingly, it is possible to provide an auxiliary artificial heart system which exhibits higher operational stability.

Although the present invention has been explained in conjunction with the above-mentioned embodiments heretofore, the present invention is not limited to the above-mentioned embodiments. Various modifications are conceivable without departing from the gist of the present invention, and the following modifications are conceivable, for example.

(1) In the above-mentioned embodiments 1 to 3, the present invention is explained by taking the slide device which is used in an aqueous liquid containing a blood component in a state where the fixed-side slide member and the rotary-side slide member are brought into contact with each other as an example. However, the present invention is not limited to such a slide device. For example, the slide device may be a slide device which further includes an intermediate slide member positioned between the fixed-side slide member and the rotary-side slide member and is used in an aqueous liquid containing a blood component in a state where the fixed-side slide member and the rotary-side slide member face each other in an opposed manner with the intermediate slide member interposed therebetween. The slide device of the present invention is preferably applicable to the above-mentioned slide device. As the intermediate slide member, for example, a slide member made of carbon, one selected from a group consisting of a variety of ceramics (for example, silicon carbide), one selected from a group consisting of a variety of plastics (for example, PTFE), one selected from a group consisting of a variety of sintered hard alloys or the like can be used. When the intermediate slide member is made of silicon carbide, it is preferable to use an intermediate slide member to which running-in treatment is applied.

(2) In the above-mentioned respective embodiments, the present invention is explained by taking the case where the pump is the auxiliary artificial heart pump as an example. However, the present invention is not limited to such an auxiliary artificial heart pump. The present invention is also applicable to a pump other than the auxiliary artificial heart pump such as, for example, a non-embedded pump used for moving blood, a pump used in a device for manufacturing medicines from an aqueous liquid containing a blood component or the like.

EXPLANATION OF SYMBOLS 1, 2, 3, 901: slide device
10, 310, 910: fixed part
12, 312, 912: fixed-side slide member,
14: slide surface (of fixed-side slide member)
15, 55: hydrate of silicon oxide
20, 50, 320, 920: rotary part
22, 52, 322, 922: rotary-side slide member
24, 54: slide surface (of rotary-side slide member)
26, 56, 926: impeller
28, 58, 328, 928: rotary shaft
30, 330, 930: drive part
40, 340: cool sealing liquid circulating part
42: cool sealing liquid inlet
44: cool sealing liquid outlet
100: auxiliary artificial heart system
110, 900: auxiliary artificial heart pump
120, 130: artificial blood vessel
140: cable
300: experiment device
326, 352: magnet
332: motor
334: torque detecting part
342: tank
344: pump
350: load adjusting part

The invention claimed is:
1. A slide device comprising:
a fixed-side slide member having a slide surface; and
a rotary-side slide member having a slide surface,
the slide device configured for being used in an aqueous liquid containing a blood component in a state where the slide surface of the fixed-side slide member and the slide surface of the rotary-side slide member face each other in an opposed manner,
wherein
at least one of the fixed-side slide member and the rotary-side slide member is formed of a member which is made of a material containing silicon and has hydrate of silicon oxide on the slide surface thereof,
the silicon oxide is oxide of silicon derived from silicon which the slide member contains, the slide member being made of a silicon-containing material,
the slide member made of a silicon-containing material is subjected to treatment for forming the hydrate of silicon oxide on the slide surface before the slide member made of a silicon-containing material is incorporated into the slide device,
the treatment for forming the hydrate of silicon oxide on the slide surface is running-in treatment, one of the fixed-side slide member and the rotary-side slide member is formed of a slide member made of silicon carbide as a slide member made of a silicon-containing material, and the other of the fixed-side slide member and the rotary-side slide member is formed of a slide member made of carbon, the slide member made of carbon is formed of a slide member made of carbon to which running-in treatment is not applied, and an average surface roughness of the slide surface of the slide member made of silicon carbide is set smaller than an average surface roughness of the slide surface of the slide member which is made of carbon.

2. The slide device according to claim 1, wherein the average surface roughness of the slide surface of the slide member made of carbon falls within a range of 0.01 µm to 1.0 µm.

3. The slide device according to claim 1, wherein the slide device is a slide device configured to be used in an aqueous liquid containing a blood component in a state where the fixed-side slide member and the rotary-side slide member are brought into contact with each other.

4. A mechanical seal provided with the slide device according to claim 1.

5. A pump comprising: a mechanical seal provided with a slide device, wherein the slide device includes:
a fixed-side slide member having a slide surface; and
a rotary-side slide member having a slide surface, the slide device configured for being used in an aqueous liquid containing a blood component in a state where the slide surface of the fixed-side slide member and the slide surface of the rotary-side slide member face each other in an opposed manner, wherein at least one of the fixed-side slide member and the rotary-side slide member is formed of a member which is made of a material containing silicon and has hydrate of silicon oxide on the slide surface thereof, the silicon oxide is oxide of silicon derived from silicon which the slide member contains, the slide member being made of a silicon-containing material, the slide member made of a silicon-containing material is subjected to treatment for forming the hydrate of silicon oxide on the slide surface before the slide member made of a silicon-containing material is incorporated into the slide device, the treatment for forming the hydrate of silicon oxide on the slide surface is running-in treatment, one of the fixed-side slide member and the rotary-side slide member is formed of a slide member made of silicon carbide as a slide member made of a silicon-containing material, and the other of the fixed-side slide member and the rotary-side slide member is formed of a slide member made of carbon, the slide member made of carbon is formed of a slide member made of carbon to which running-in treatment is not applied, and an average surface roughness of the slide surface of the slide member made of silicon carbide is set smaller than an average surface roughness of the slide surface of the slide member which is made of carbon.

6. The pump according to claim 5, wherein the pump is an auxiliary artificial heart pump.

7. An auxiliary artificial heart system comprising:
a pump, wherein
the pump is an auxiliary artificial heart pump,
the pump comprises a mechanical seal provided with a slide device,
the slide device includes
a fixed-side slide member having a slide surface; and
a rotary-side slide member having a slide surface, the slide device configured for being used in an aqueous liquid containing a blood component in a state where the slide surface of the fixed-side slide member and the slide surface of the rotary-side slide member face each other in an opposed manner, at least one of the fixed-side slide member and the rotary-side slide member is formed of a member which is made of a material containing silicon and has hydrate of silicon oxide on the slide surface thereof, the silicon oxide is oxide of silicon derived from silicon which the slide member contains, the slide member being made of a silicon-containing material, the slide member made of a silicon-containing material is subjected to treatment for forming the hydrate of silicon oxide on the slide surface before the slide member made of a silicon-containing material is incorporated into the slide device, the treatment for forming the hydrate of silicon oxide on the slide surface is running-in treatment, one of the fixed-side slide member and the rotary-side slide member is formed of a slide member made of silicon carbide as a slide member made of a silicon-containing material, and the other of the fixed-side slide member and the rotary-side slide member is formed of a slide member made of carbon, the slide member made of carbon is formed of a slide member made of carbon to which running-in treatment is not applied, and an average surface roughness of the slide surface of the slide member made of silicon carbide is set smaller than an average surface roughness of the slide surface of the slide member which is made of carbon.

* * * * *